United States Patent [19]
Forat et al.

[11] Patent Number: 5,354,439
[45] Date of Patent: Oct. 11, 1994

[54] PROCESS FOR THE SYNTHESIS OF FLUORINATED DERIVATIVES

[75] Inventors: Gerard Forat; Laurent Gilbert; Bernard Langlois, all of Lyons, France

[73] Assignee: Rhone-Poulenc Chimie, Courbevoie, France

[21] Appl. No.: 730,171

[22] Filed: Jul. 16, 1991

[30] Foreign Application Priority Data

Jul. 16, 1990 [FR] France ............................ 90 09023
Jul. 16, 1990 [FR] France ............................ 90 09025

[51] Int. Cl.$^5$ ............................................... C07C 17/00
[52] U.S. Cl. ............................ 204/157.6; 204/157.62; 204/157.94; 204/157.97
[58] Field of Search .................. 204/157.62, 157.94, 204/157.6, 157.62, 157.94, 157.97

[56] References Cited

U.S. PATENT DOCUMENTS

| 2,229,365 | 10/1980 | Oeser et al. | 260/465 G |
| 4,140,719 | 2/1979 | Tull et al. | 260/580 |
| 4,484,993 | 5/1984 | Ishikawa et al. | 204/158 HA |

FOREIGN PATENT DOCUMENTS 2391990 12/1978 France.

OTHER PUBLICATIONS

Chemical Abstract No. 110:74753n.

*Primary Examiner*—John Niebling
*Assistant Examiner*—C. Delacroix Muirheid
*Attorney, Agent, or Firm*—Finnegan, Henderson, Farabow, Garrett & Dunner

[57] ABSTRACT

A process for the synthesis of fluorinated organic compounds and a reagent suitable for use in the process. The process is carried out by exchange with fluorides, while preferably agitating the reaction medium with ultrasonic sound.

45 Claims, 1 Drawing Sheet

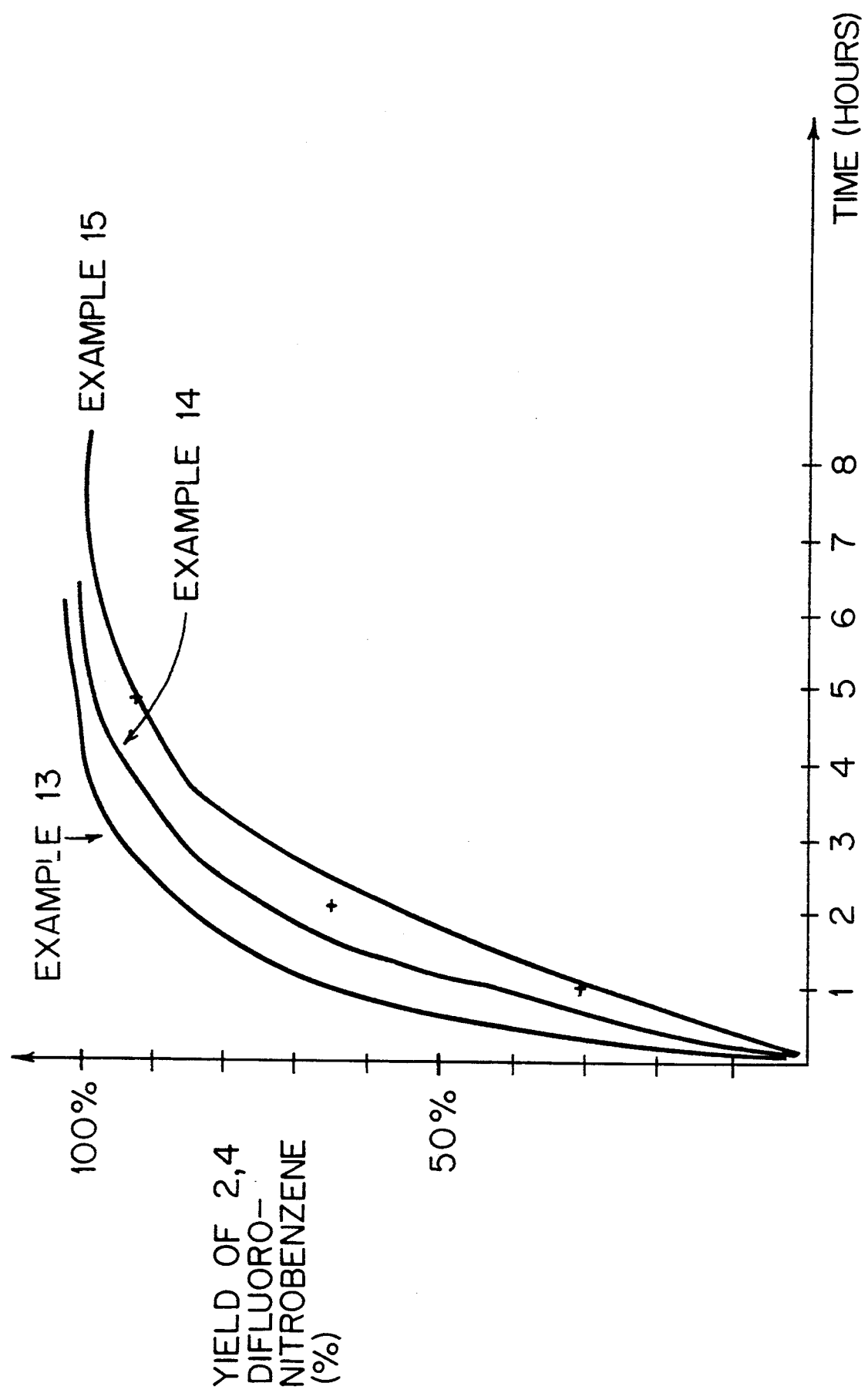

PROCESS FOR THE SYNTHESIS OF FLUORINATED DERIVATIVES

The present invention relates to the synthesis of fluorinated derivatives. It relates more particularly to the synthesis of fluorinated derivatives from halogenated derivatives such as chlorinated derivatives.

Fluorinated compounds are generally difficult to obtain. The reactivity of fluorine is such that it is not possible to obtain the fluorinated derivatives directly.

One commonly used technique for producing fluorinated derivatives comprises a reaction in which in a halogenated or sometimes nitrated derivative, generally a chlorinated derivative the halogen or nitrogen is replaced with an inorganic fluoride. The inorganic fluoride is often a fluoride of an alkali metal, which generally has a high atomic weight. In many cases, potassium fluoride is used, since it represents a satisfactory economic compromise.

Under these conditions, numerous processes, such as those described in French certificate of addition No. 2 353 516 and in the article Chem. Ind. (1978)–56, have been described and used industrially to obtain aryl fluorides. Electron-attracting groups are grafted to the aryl fluorides. This technique has disadvantages when the substrate is not particularly suited to this type of synthesis. The main disadvantages of this technique will be analyzed below.

The reaction has been found to be slow and, because of a long residence time, has been found to require significant investment. Furthermore, in order to be commercially useful, this technique has been used at high temperatures, which are typically about 250° C., i.e. in the zone where the most stable organic solvents start to decompose.

Finally, it has been found that the yield is poor, unless particularly expensive reagents are used, such as fluorides of an alkali metal having an atomic mass higher than that of potassium.

Because of the cost of these alkali metals, their industrial use is only appropriate for products having a high added value or when justified by improvement in the yield and in the kinetics, which is rare.

For this reason, one of the objects of the present invention is to provide a technique which facilitates exchange between halogens such as chlorine and fluorine, while significantly improving the exchange efficiency.

Another object of the present invention is to provide a technique which improves the exchange kinetics sufficiently to permit the use of a temperature which is significantly lower than that previously employed. This reduction in temperature will have to be sufficient to permit the use of reagents which were not previously used because of their instability at the temperature at which the exchange took place.

Another object of the present invention is to provide a process for exchange between fluorine and halogens of higher atomic number using this technique.

Additional objects and advantages of the invention will be set forth in part in the description that follows, and in part will be obvious from the description, or may be learned by practice of the invention. The objects and advantages of the invention may be realized and attained by means of the instrumentalities and combinations particularly pointed out in the appended claims.

These objects and others which will become apparent are achieved by a process for the synthesis of fluorinated organic compounds which involves an exchange with inorganic fluorides, wherein the exchange is effected by using ultrasonic sound. Surprisingly, it has been found that the reaction for exchange between the fluoride ion in the form of an alkali metal or alkaline-earth metal fluoride with a halogen ion having a higher order (i.e. having a higher atomic number) bonded to a carbon, the latter being either aromatic or aliphatic, was significantly improved by the use of ultrasonic sound.

This is particularly surprising, both because experiments were previously conducted and proved to be negative (cf. "HALEX" FLUORINATION OF CHLORINATED BENZALDEHYDES AND BENZOYL CHLORIDES Journal of Fluorine Chemistry, 46, (1990) 529–537); and also LAW OFFICES because ultrasonic sound is generally used for reactions which take place at low temperature and in a dilute medium (cf. Sonochemistry—The Use of Ultrasonic Waves in Synthetic Organic Chemistry, Cathy EINHORN, Jacques EINHORN, Jean-Louis LUCHE in Synthesis [Journal of Synthetic Organic Chemistry] p. 787)

By contrast, in the method of the present invention, the ultrasonic sound is preferably used at a relatively high temperature, i.e. a temperature which is significantly higher than ambient temperature. In general, the temperature is at least 100° C. (unless otherwise stated, the zeros are not significant numbers).

It is not possible to precisely determine why the experiment mentioned in the literature did not provide a satisfactory result. However, the use of ultrasonic sound can give improved results under the preferred conditions. It is also possible that the ultrasonic cell used in the above-mentioned article could have caused the failure.

In fact, in order to obtain preferred results, the power of ultrasonic sound emitted directly by the wall providing this emission should be at least 20 and is preferably at least 50 W/ cm$^2$. It is more preferably at least 100 W/cm$^2$ and even more preferably 200 W/cm$^2$.

The existence of a lower limiting value for the power is even more important when an ultrasonic cell is used in which the ultrasonic sound is not transmitted directly by a probe but is instead transmitted through the wall of the vessel and through the mixture in which it is immersed and in which the reaction takes place.

In the present invention, the transmission is direct if the active part of the probe is not separated from the reaction mixture by a liquid.

There is no upper limiting value for the power; any power used commercially is suitable for activating this exchange reaction. However, it is preferable to select a power such that the vessel in which the reaction takes place is not rendered brittle by ultrasonic sound.

The frequencies which can be used are those produced by commercially available equipment. Thus, the frequency of the ultrasonic sound preferably ranges from 10 to 100 kHz, more preferably from 15 to 50 kHz.

However, some frequencies give significantly better results. These preferred frequencies depend on the reaction mixture and on the conditions of use. The preferred frequencies correspond to the resonance frequencies of the mixture under the experimental conditions.

The resonance frequencies can be determined easily by those skilled in the art. They are the frequencies corresponding to the energy absorption maxima of the mixture. Simple frequency scanning, preferably at maximum power, enables the energy absorption peaks to be determined.

Searching for the best absorption is not critical. In fact, conventional equipment emits a spectrum which is sufficiently wide to include at least one resonant frequency. However, if a generator is used which gives a very pure ultrasonic wave, such searching will be useful or even necessary in order to fully realize the desired advantages.

Preferably, the spectrum of the emitted ultrasonic wave partly contains at least one resonance frequency.

The use of such a technique has enabled reactions which with conventional techniques took place only at very high temperatures, i.e. about 250° C., to be carried out with very good yields at temperatures ranging from 100° to 200° C., preferably from 100° to 150° C.

The volume in which the reaction is accelerated is relatively small and is determined by a cylinder defined by the effective surface area of the probe and a generatrix normal to the surface of the probe, the length of which does not exceed approximately 10 or preferably 5 cm. It appears that the reaction is faster when the reaction mixture is closer to the probe. A highly effective volume may therefore be regarded as a volume defined by the surface area of the probe and a generatrix having a size from 1 to 5 cm.

The agitation method and/or the chemical engineering techniques which are used to implement the present invention must account for this effective volume and must permit the essential part of the reaction mixture to pass into this effective volume numerous times.

If the process is carried out discontinuously (i.e. batchwise), the ratio between the volume of the reaction mixture and the effective volume (or the time ratio) is at most about 20, preferably about 10 and more preferably about 5. During continuous or pulse operation, the residence time and/or the pulse time in the effective volume must be taken into account.

The process according to the present invention is most efficient when the above conditions are combined.

Preferably, the reaction takes place in a mixture comprising:
a dipolar aprotic solvent or reagent; and
a solid phase comprising an alkali metal fluoride, and if appropriate, at least one cation for promoting the reaction.

This mixture itself provides a significant improvement over the prior art even without the use of ultrasonic sound.

The proportion of solid in the mixture, which is defined as mass of solid material relative to the total mass, is preferably at least 2/5, more preferably ½ and even more preferably 2/3, or relative to the mass of the reaction mixture, preferably at least 1/5, ¼ and ⅓ respectively.

The reagent preferably comprises, as a promoter, an alkali metal cation which is heavier than potassium. This alkali metal cation may be introduced in the form of a halide and is not necessarily in the form of a fluoride. In general, the alkali metal cation is introduced in the form of a chloride. The alkali metal cation content preferably ranges from 1 to 5 mol% and more preferably from 2 to 3 mol% of the alkali metal fluoride used.

The reagent may contain, as a promoter, agents which are often referred to as phase transfer agents. These phase transfer agents are "oniums", i.e. compounds which have a name containing the suffix "onium". The oniums generally represent from 1 to 10 mol% and preferably from 2 to 5 mol% of the alkali metal fluoride.

Preferred oniums include tetraalkylammoniums having 4 to 12 carbon atoms and more preferably 4 to 8 carbon atoms. The tetraalkylammonium is in general tetramethylammonium.

The term alkyl is taken in the accepted meaning "lato sensu" given in the DUVAL chemical dictionary.

The tetraalkylammoniums have the disadvantage of having low stability at temperatures above about 150° C. One advantage of the present invention is that it permits reactions at temperatures below or close to this value. This permits the use of the ammoniums, in particular tetramethylammonium.

The amount of tetraalkylammonium cation generally ranges from 1 to 10% and preferably from 2 to 5% of the mass of the alkali metal fluoride.

The dipolar aprotic solvent which can be used must have a significant dipolar moment. Thus, its relative dielectric constant $\epsilon$ is at least about 10 (once again, the zeros are not regarded as significant figures in the present description, unless specified otherwise). Preferably, $\epsilon$ is less than or equal to 100 and greater than or equal to 25.

In the present invention, the best results were obtained when dipolar aprotic solvents which had a donor index DN of between 10 and 50 were used. The donor index DN is defined as the $\Delta H$ (enthalpy difference), expressed in kilocalories (Kcal), of the combination of the dipolar aprotic solvent with antimony pentachloride in methylene chloride.

The oniums are chosen from the group of cations formed by the elements of columns V B and VI B (as defined in the table of the periodic classification of the elements published as a supplement to the Bulletin de la Societe Chimique de France (Bulletin of the French Chemical Society) in January 1966) with, respectively, 4 or 3 hydrocarbon chains. The present invention includes the use of derivatives in which one chain or even several chains are replaced by one or more unsaturations, since they are regarded as stable under the reaction conditions.

The particle size plays a relatively minor role in the kinetics if the particle size is not too fine, i.e. if the majority of particles are larger than one micron and the majority of particles are smaller than 250 microns. However, it has been shown that the particle size can influence the kinetics. Thus, it is desirable that the suspended solid has a particle size such that its $d_{90}$ (defined as the mesh allowing 90% by weight of the solid to pass through) is at most 100 micrometers, preferably at most 50 $\mu m$ and more preferably at most 20 82 m. Preferably, the lower limit of the particle size is such that the $d_{10}$ of the suspended solid is at least 0.1 $\mu m$ and more preferably at least 1 $\mu m$.

In general, the molar ratio of the alkali metal fluoride to the substrate ranges from 1:1 to 1.5:1 and is preferably about 1.25:1 relative to the stoichiometric amount. This ratio is, however, generally not critical since it permits suitable agitation of the reagent.

According to the present invention, it is desirable that the water content of the reagent is at most about 2% and preferably 1% relative to the mass of the reagent (mass ratio).

The agitation is preferably conducted in such a way that at least 80% and more preferably at least 90% of the solids are kept in suspension. In general, the agitation caused by the ultrasonic sound is sufficient in the zone where the ultrasonic sound is active.

It is desirable that the bulk of the solid is in suspension in the reaction mixture. Thus, in order to meet this constraint, the agitation must be neither too vigorous nor too weak. If the agitation is too vigorous there is a risk that an excessive amount of solid will stick against the wall of the reactor as a result of cyclone effects. If the agitation is too weak, the solids resulting from the reaction and the solids used as fluorine source will not go into suspension.

The exchange reaction may use any fluoride known by those skilled in the art to be a good exchange reagent. However, alkali metal cations having an order at least equal to that of potassium are preferred. It is also possible to use non-alkali metal cations having equivalent properties, such as tetraalkylammonium fluorides.

A preferred embodiment of the present invention comprises a process having the following steps:

a) Mixing the reagents.

b) Subjecting the mixture obtained by step a) to at least one reaction step under ultrasonic sound.

c) Separating the liquid and solid phases.

d) Treating the liquid phase obtained in step c) to recover the final product and also the solvent containing the unreacted starting material.

e) Recycling the solvent and the unreacted starting material obtained in step d) back to step a).

f) An optional step involving treatment of the solid phase originating from step c) in order to regenerate the alkali metal fluoride and recycling to step a).

The use of ultrasonic sound releases a significant amount of energy within the reaction mixture. This energy completely or partially replaces the heating which is usually required.

The present invention permits a very significant advance in the use of solvents.

Under some circumstances, it may be preferable that some of the solids in the reagent, and thus in the reaction mixture, consist of an inert material having a particle size meeting the constraints specified above. Such circumstances include cases where heavy (molecular mass $\geq 200$) or very heavy (molecular mass $\geq 500$) molecules are treated. By using ultrasonic agitation, those skilled in the art may avoid constraints involving stability at high temperatures and the high boiling point of the solvents used. During the exchange between fluorine and a halogen of higher order, it is preferable not to work at a temperature very close to the boiling point of the mixture, with a difference of at least 10° C.

This opens up particularly interesting prospects for separating the solvents from the starting reagents and the products produced and facilitates recycling of the reaction mixtures. It is then possible to regenerate the fluorine source if the associated cation is expensive, as in the case of cesium.

This method of the present invention may be used to replace a halogen or equivalent, both on an aliphatic carbon and on an aromatic carbon.

If the radical is an aryl, it is preferably deficient in electrons and has an electron density at most equal to that of benzene and preferably at most close to that of a halobenzene. This deficiency may be due to the presence of a heteroatom in the aromatic (generally hexagonal) ring, such as pyridine or quinoline. Of course, the electron deficiency may also be caused by electron-attracting groups. The deficiency in electrons may also be due to both of these two causes.

Thus, the aryl preferably has at least one substituent on the same ring as that containing the chlorine or equivalent. The substituent is preferably chosen from the groups which attract by an inductive effect or by a mesomeric effect, as defined in the organic chemistry reference publication "Advanced Organic Chemistry" by M. J. MARCH, 3rd edition, publisher WILLEY, 1985, (cf. in particular pages 17 and 238) with the exception of the groups capable of interacting with the fluoride ions (essentially the groups carrying hydrogen and capable of giving hydrogen bonds). The following are examples of attracting groups: $NO_2$, $CF_3$, CN, COX (X=Cl, Br, F, OR), CHO, Cl and Br.

The Hammett constant of the attracting group is at least equal to 0.1, and is preferably greater than or equal to 0.2. More precisely, $\Sigma\sigma_p$ is greater than or equal to the above values. In this formula, which employs mathematical symbols, $\Sigma$ is defined as the arithmetic sum of the Hammett constants of the nucleus in question is calculated. Strictly speaking, it would be appropriate to write, according to the symbols, $$\sum_{i=1}^{i=n} \sigma_p{}^i$$

where n is the top number of the nucleus in question)

Since the effect of the substituent on the nucleus is not completely uniform over the various positions, and since the Hammett constant therefore varies slightly depending on the position of the summit in question in relation to the substituent, the constant $\sigma_p$ of the para position is chosen for doing the calculation when the substituent is alone. For further details on Hammett constants, reference may be made to various works and especially to the work of a general nature above (pages 242 to 250), which also give the values of $\sigma_p$ for the most common groups (page 244). There is no upper value for $\sigma_p$, except that it rarely exceeds 2 and very rarely exceeds 3.

The process for the synthesis of aryl fluoride from halogenated compounds by an exchange reaction between the halogen, comprises contacting the halogenated compound with a reagent comprising:

a dipolar aprotic solvent;

a solid phase consisting at least partially of alkali metal fluoride; and if appropriate, a cation promoter;

the solids content, which is defined as mass of solid material relative to the mass of the reaction mixture, being preferably at least 1/5, more preferably ¼ and most preferably ⅓, on condition that if at the same time the dipolar organic solvent is sulfolane and a cation promoter is not present, the solids content is, respectively, at least ⅓ (when the molar ratio between the substrate and the sulfolane is higher than 0.5) and 2/5 (when the molar ratio between the substrate and the sulfolane is higher than 1).

This reagent gives good results even without ultrasonic sound.

As mentioned above, the agitation is preferably carried out in such a way that at least 90% of the solids are kept in suspension. In fact, it is desirable for the bulk of the solids to be in suspension in the reaction mixture. Thus, the agitation must be neither too vigorous nor too weak. If the agitation is too vigorous, it is possible that an excessive amount of solids will adhere to the wall of the reactor as a result of cyclone effects. If the agitation is too weak, it will be incapable of suspending the solids resulting from the reaction and the solids used as fluorine source. Devices such as those described in the European Patent Application No. 115 559 A1, which is expressly incorporated by reference herein, permit good agitation with low energy consumption.

BRIEF DESCRIPTION OF THE DRAWINGS

The single Figure is a plot of the yield as a function of time for the reactions conducted in Examples 12, 13 and 14.

DESCRIPTION OF THE PREFERRED EMBODIMENTS

Reference will now be made in detail to the present preferred embodiments of the invention. In the examples and throughout the specification and claims, all parts and percentages are by weight unless otherwise specified.

The following non-limiting examples illustrate the invention.

EXAMPLE 1

The following were charged into a 70 ml reactor under a nitrogen atmosphere:
17.7 g (306 mmoles) of potassium fluoride,
1.3 g (12 mmoles) of tetramethylammonium chloride,
17.0 g of dimethyl sulfoxide, and
19.6 g (102 mmoles) of 2,4-dichloronitrobenzene.

The reaction mixture was treated with ultrasonic sound, while the temperature was maintained at 130° C. for 30 minutes.

After filtration, an analysis of the crude reaction product gave the following results:
conversion of 2,4-dichloronitrobenzene: 67.1%
yield of fluorochloronitrobenzenes : 52%
yield of 2,4-difluoronitrobenzene : 13.9%

EXAMPLE 2

The same method was used as in Example 1. The reaction mass was not subjected to the action of ultrasonic sound but was heated at 130° C. for 30 minutes:
conversion of 2,4-dichloronitrobenzene: 43.8%
yield of fluorochloronitrobenzenes : 34.3%
yield of 2,4-difluoronitrobenzene : 4.0%

EXAMPLES 3 and 4

Two comparative examples identical to the cases of Examples 1 and 2 were carried out using the fluorinating mixture KF+CsF (3%) in sulfolane at 130° C. for thirty-five minutes:

| Example No. | Ultrasonic sound | Conversion % | Yield 2,4-DiFNB % | Yield of monofluorinated compounds |
| --- | --- | --- | --- | --- |
| 3 | YES | 38.4 | 3.4 | 34 |
| 4 | NO | 3.2 | 0 | 2.3 |

EXAMPLE 5

The following were charged into a 30 ml reactor closed with a septum, under a nitrogen atmosphere:
4.06 g of KF (70 mmoles),
0.3 g of Me$_4$NCl (2.7 mmoles),
5.63 g of 2,4-dichloronitrobenzene (29.3 mmoles), and
8.16 of dimethyl sulfoxide.

The mixture was treated with ultrasonic sound in cycles. For 75% of each 1-second cycle, the ultrasonic sound was inactive.

The temperature was kept at 130° C. for 30 minutes.
Conversion of 2,4-dichloronitrobenzene : 84%
Yield of fluorochloronitrobenzene : 47%
Yield of 2,4-difluoronitrobenzene : 34%

EXAMPLE 6

The following were charged into a 30 ml reactor closed with a septum, under a nitrogen atmosphere:
8.14 g of dimethyl sulfoxide,
0.3 g of Me$_4$NCl (2.7 mmoles), and
4.03 g of KF (70 mmoles).

This mixture was pre-treated with ultrasonic sound for 10 minutes, keeping the temperature at 50° C. The ultrasonic sound was stopped and 5.7 g (29.7 mmoles) of 2,4-dichloronitrobenzene were then injected rapidly, keeping the temperature at 130° C. by conventional heating.

After 30 minutes, the following were obtained:
Conversion of 2,4-dichloronitrobenzene : 79%
Yield of fluorochloronitrobenzene : 49%
Yield of 2,4-difluoronitrobenzene : 30%

EXAMPLE 7

A 250 ml cylindrical glass reactor was fitted with an anchor stirrer, an ascending condenser, a thermometer sleeve, a dip tube and an inlet tube.

These two tubes were connected to a second 30 ml stainless steel reactor surmounted by an ultrasonic probe, the latter serving, via a pump, to circulate the reaction mixture between the 2 reactors at an average flow rate of 30 l/h.

The following were charged into the glass reactor:
150 g of dimethyl sulfoxide,
75 g of KF (1.29 moles),
99.3 g of 2,4-dichloronitrobenzene (0.52 mole), and
4.8 g of Me$_4$NCl.

The reaction mixture was heated to 130° C., agitated, circulated between the two reactors and treated with ultrasonic sound by 50% pulses. The duration of the experiment was 1 h 30 minutes.
Conversion of 2,4-dichloronitrobenzene 99%
Yield of fluorochloronitrobenzene 18.8%
Yield of 2,4-difluoronitrobenzene 73.5%

EXAMPLE 8

A comparative experiment was carried out in the 250 ml reactor but heated only in a conventional manner. In other words, no ultrasonic agitation was used. After 1 h 30 minutes at 130° C., the following results were obtained:
Conversion of 2,4-dichloronitrobenzene: 83%
Yield of fluorochloronitrobenzene : 35.2%
Yield of 2,4-difluoronitrobenzene : 39.5%

EXAMPLE 9

The following were charged into a 50 ml reactor under a nitrogen atmosphere:
5.8 g of KF (100 mmoles),
0.43 g of Me$_4$NCl (0.4 mmole),
7.75 g of 2,4-dichloronitrobenzene (40.3 mmoles), and
11.6 g of dimethyl sulfoxide.

The reaction mixture was treated with ultrasonic sound, optimizing the ultrasonic frequency as a function of the resonance frequency of the system. Thus, the ultrasonic sound was allowed to act for 30 seconds at a frequency of 20,350 Hz at 130° C. The following results were obtained:
Conversion of 2,4-dichloronitrobenzene : 81.5%
Yield of chlorofluoronitrobenzene : 48%
Yield of 2,4-difluoronitrobenzene

EXAMPLE 10

The following were charged into a 50 ml reactor under a nitrogen atmosphere:
5.8 g of KF,
0.43 g of Me$_4$NCl,
7.75 g of 2,4-dichloronitrobenzene, and
11.6 g of dimethylnitrobenzene sulfoxide.

The reaction mixture was treated with ultrasonic sound at 150° C. for 30 minutes. The following were obtained:
Conversion of 2,4-dichloronitrobenzene : 99%
Yield of chlorofluoronitrobenzene : 15%
Yield of 2,4-difluoronitrobenzene : 80%

EXAMPLE 11

The following were charged into a 30 ml reactor under a nitrogen atmosphere:
2.9 g of KF (50 mmoles),
0.75 g of Ph$_4$PCl (2 mmoles),
4 g of 4-chloronitrobenzene (25.5 mmoles), and
12 g of dimethyl sulfoxide.

The reaction mixture was treated with ultrasonic sound at 170° C. for 1 hour.
Conversion of 4-chloronitrobenzene : 60%
Yield of 4-fluoronitrobenzene : 54%

EXAMPLE 12

The reagents were charged in an identical manner into the same reactor but the mixture was heated by conventional means at 170° C. for 1 hour with magnetic stirring.
The following were obtained:
Conversion of 4-chloronitrobenzene : 39%
Yield of 4-fluoronitrobenzene : 34%

The examples show the value of the mixture according to the invention even without the use of ultrasonic sound.

EXAMPLE 13

A suspension of potassium fluoride (174 g, 3 moles) and tetramethylammonium chloride (13 g, 0.12 mole) in dimethyl sulfoxide (176 g, 2.26 moles) was charged into a 1 l reactor, preheated to 50° C. and placed under a nitrogen atmosphere. This suspension had previously been ground for 30 minutes in a type LME 1 Netzch ball mill. Before grinding, the suspension had the following particle size characteristics:
average size: 65 μm, d$_{10}$:24 μm, d$_{90}$:140 μm.
After grinding, the particle size characteristics were:
average size 11 μm, d$_{10}$: 2 μm, d$_{90}$: 22 μm.
Unless indicated to the contrary, the potassium fluoride used contains less than 100 ppm of water and the solvent about 50 ppm of water.
2,4-Dichloronitrobenzene (230.4 g, 1.2 moles) was then introduced.
The mixture was agitated to keep all of the solid in suspension. After heating for 3 h 30 minutes at 130° C. an analysis of the reaction mixture revealed that the conversion of 2,4-dichloronitro-benzene was complete, that the yield of 2,4-difluoronitrobenzene was 92% and that the yield of fluorochloronitrobenzene was 8%. This mixture of monofluoromonochloro isomers was predominantly 4-fluoro.

The reactor was then cooled to 30° C. and the reaction mixture was diluted using 100 ml of methylene chloride. The mixture was stirred for 10 minutes and passed through a glass sinter. The reactor and the precipitate were rinsed twice with 100 ml of methylene chloride. The filtrate was recovered and the methylene chloride was evaporated with the aid of a rotary evaporator (bath temperature=70° C., p=100 mm Hg). The DMSO was removed by washing with water and the residue was distilled. 173.6 g of 2,4-difluoronitrobenzene (yield 91%, purity >99%) were thus obtained.

EXAMPLE 14

A procedure analogous to that described in Example 13 but using unground potassium fluoride as the starting material leads, after heating for 4 h 30 at 130° C., to the following results:
Conversion of 2,4-dichloronitrobenzene =99.7%.
Yield of 2,4-difluoronitrobenzene=90.4%.
Yield of fluorochloronitrobenzenes =9.7%.
After treatment and distillation, 173.9 g of product (yield of 2,4-difluoronitrobenzene 87.4%, purity 96.3%) were obtained.

EXAMPLE 15

A procedure analogous to that described in Example 13, using an unground potassium fluoride and 378 g (4.85 moles) of dimethyl sulfoxide as the starting materials, leads, after heating for 6 h at 130° C., to the following results:
Conversion of 2,4-dichloronitrobenzene =100%.
Yield of 2,4-difluoronitrobenzene =93.4%.
Yield of fluorochloronitrobenzenes=1%.

The comparison of the kinetics of the experiments corresponding to Examples 13, 14 and 15 is shown in the single Figure, which illustrates the yield of 2,4-difluoronitrobenzene as a function of time.

EXAMPLE 16

The reaction was carried out in a 100 ml reactor, placed under a nitrogen atmosphere, into which the following were introduced successively:
28 g of potassium fluoride (0.048 mole),
1.8 g of cesium fluoride (12 mmoles),
28 g of 2,4-dichloronitrobenzene (0.146 mole) and 60 g of sulfolane.

The reaction mixture was heated 180° C. while maintaining an agitation such that the solid was kept in suspension. After heating for 6 h, the following results were obtained:
Conversion of 2,4-dichloronitrobenzene=100%.
Yield of 2,4-fluoronitrobenzene=95%.
Yield of fluorochloronitrobenzenes=5%.

EXAMPLE 17

2.4 g of potassium fluoride (41.4 mmoles), 3.9 g of 2,4-dichloronitrobenzene (20.5 mmoles) and 6 g of sulfolane were charged into a 50 ml reactor placed under a nitrogen atmosphere.

The mixture was heated at 180° C. for 11 hours. The reaction mixture was then filtered and the filtrate analyzed by GPC:
Conversion of 2,4-dichloronitrobenzene =85.5%.

Yield of 2,4-difluoronitrobenzene=29.0%.
Yield of fluorochloronitrobenzenes : 44.7%.

EXAMPLES 18 to 20

The method of Example 17 was repeated with the addition of a catalytic amount of water at the start of the experiment.

| Example No. | % $H_2O$ (by weight) | Conversion of 2,4-DiClNB (%) | Yield of 2,4-DiFNB (%) | Yield of mono-fluorinated compounds |
| --- | --- | --- | --- | --- |
| 18 | 0.4 | 84.2 | 26.8 | 47.5 |
| 19 | 1.1 | 83.1 | 25.5 | 45.3 |
| 20 | 2.6 | 41.8 | 4.5 | 27.0 |

EXAMPLE 21

2.6 g of potassium fluoride (45.2 mmoles), 2.96 g of 2,4-dichloronitrobenzene (5.4 mmoles) and 6.2 g of DMSO were charged into a 50 ml reactor placed under a nitrogen atmosphere.

The mixture was heated at 130° C. for 6 h. The reaction mixture was then filtered and the filtrate analyzed by GPC:
Conversion of 2,4-dichloronitrobenzene : 71%
Yield of 2,4-difluoronitrobenzene : 21.8%
Yield of 4-fluoro-2-chloronitrobenzene : 11.9%
Yield of 2-fluoro-4-chloronitrobenzene : 39.6%.

EXAMPLES 22 to 26

The method of Example 21 was repeated with the addition of a catalytic amount of various oniums:

| Ex. No. | Onium | Onium (molar %) KF | Conversion of 2,4-DiClNB (%) | Yield of 2,4-DiFNB (%) | Yield of mono-fluorinated compounds (%) |
| --- | --- | --- | --- | --- | --- |
| 22 | $Me_4NCl$ | 2.15 | 100 | 93.1 | 1.8 |
| 23 | $Ph_3SCl$ | 3.87 | 8.9 | 65.6 | 18.6 |
| 24 | $Ph_4AsCl$ | 3.92 | 100 | 66.6 | 0.6 |
| 25 | $BzMe_3NBr$ | 4.1 | 99.9 | 76.8 | 9.2 |
| 26 | $BzMe_3NHF_2$ | 4.4 | 98.7 | 71.5 | 18.0 |

EXAMPLES 27 to 29

The method of Example 22 was repeated for various solvents:

| Example No. | SOLVENT | Conversion of 2,4-DiClNB (%) | Yield of 2,4-DiFNB (%) | Yield of mono-fluorinated compounds (%) |
| --- | --- | --- | --- | --- |
| 27 | Sulfolane | 100 | 84.1 | 3.3 |
| 28 | DMF | 99.5 | 78.3 | 15.0 |
| 29 | DMAC | 97.2 | 55.5 | 25.5 |

EXAMPLE 30

The method of Example 17 was repeated by heating a mixture of potassium fluoride (61.5 mmoles, 3.6 g), 2,4-dichloronitrobenzene (20.5 mmoles, 3.9 g) and sulfolane (6.2 g) at 180° C. for 6 hours:
Conversion of 2,4-dichloronitrobenzene : 81.7%
Yield of 2,4-difluoronitrobenzene : 47.7%

EXAMPLES 31 to 37

The method of Example 30 was repeated with the addition of a catalytic amount of cesium fluoride, cesium chloride or rubidium fluoride.

| Example No. | Catalyst | Catalyst (molar %) KF | Conversion of 2,4DiCl-NB (%) | Yield of 2,4-DiFNB (%) | Yield of mono-fluorinated compounds (%) |
| --- | --- | --- | --- | --- | --- |
| 31 | CsF | 0.1 | 85.4 | 29.5 | 45.2 |
| 32 | CsF | 0.9 | 99.5 | 71.9 | 12.1 |
| 33 | CsF | 1.5 | 99.3 | 72.4 | 15 |
| 34 | CsF | 2.5 | 100 | 95.3 | 0 |
| 35 | CsF | 5 | 100 | 96.4 | 0 |
| 36 | CsCl | 1 | 98.6 | 64.9 | 3.1 |
| 37 | RbF | 4.7 | 98.4 | 48.2 | 7.0 |

EXAMPLE 38

The following were charged into a 50 ml reactor placed under a nitrogen atmosphere:
3 g of potassium fluoride (51.7 mmoles),
7.8 g of 2,4-dichloronitrobenzene (40.6 mmoles) and
6 g of sulfolane.

The reaction mixture was heated at 180° C. for 6 h. After cooling, the reaction mixture was filtered and the filtrate analyzed by GPC:
Conversion of 3,4-dichloronitrobenzene=4.8%
Yield of 3,4-difluoronitrobenzene=4.4%

EXAMPLES 39 to 41

The method of Example 38 was repeated under the following reaction conditions:

| Example No. | Reaction conditions | Catalyst | Catalyst KF (%) | Conversion (%) | Yield (%) |
| --- | --- | --- | --- | --- | --- |
| 39 | DMSO - 130° C. 6 h | — | — | 2.2 | 2.0 |
| 40 | DMSO - 170° C. 6 h | $Me_4NCl$ | 3.9 | 64 | 61.2 |
| 41 | Sulfolane - 180° C. 6 h | CsF | 2.6 | 28.9 | 27.5 |

It will be apparent to those skilled in the art that various modifications and variations can be made in the present invention without departing from the scope or spirit of the invention. Thus, it is intended that the present invention cover the modifications and variations of this invention provided they come within the scope of the appended claims and their equivalents.

What is claimed is:

1. A process for the synthesis of a fluorinated organic compound comprising reacting an organic compound and a fluoride compound under conditions to exchange fluorine for an atom bonded to said organic compound, wherein ultrasonic sound in the range of from 10 to 100 kHz is applied to said organic compound during said process and wherein the power transmitted to the mixture via an active surface of the probe is at least 20 $W/cm^2$.

2. The process of claim 1, wherein the fluoride is in the form of a suspended solid.

3. The process of claim 2, wherein the ultrasonic sound is transmitted directly by a probe into a reaction mixture comprising said fluoride and said organic compound.

4. The process of claim 3, wherein the power transmitted to the mixture via an active surface of the probe is at least 50 W/cm$^2$.

5. The process of claim 4, wherein said power is at least 100 W/cm$^2$.

6. The process of claim 4, wherein said power is at least 200 W/cm$^2$.

7. The process of claim 3, wherein the ultrasonic sound is emitted in a vessel containing said organic compound in such a way that fluoride particles pass through a volume defined by the surface area of the probe and a generatrix having a size ranging from 1 to 5 cm.

8. The process of claim 3, wherein the reaction mixture further comprises an alkali metal cation heavier than potassium.

9. The process of claim 8, wherein the fluoride is an alkali metal fluoride and wherein the alkali metal cation represents from 1 to 5% by weight of the mass of the alkali metal fluoride.

10. The process of claim 9, wherein the alkali metal cation represents from 2 to 3% by weight of the mass of the alkali metal fluoride.

11. The process of claim 3, wherein the reaction mixture further comprises an onium.

12. The process of claim 11, wherein the fluoride is an alkali metal fluoride and wherein the onium represents 1 to 10% by weight of the alkali metal fluoride.

13. The process of claim 12, wherein the onium represents 2 to 5% by weight of the alkali metal fluoride.

14. The process of claim 11, wherein the onium is chosen from the group of cations formed by the elements of columns V B and VI B of the periodic table of elements, said cations having, respectively, 4 or 3 hydrocarbon chains.

15. The process of claim 3, wherein the reaction mixture further comprises a tetraalkylammonium cation having 4 to 12 carbon atoms.

16. The process of claim 15, wherein the tetraalkylammonium cation has 4 to 8 carbon atoms.

17. The process of claim 2, wherein the reaction is carried out at a temperature ranging from 100° to 200° C.

18. The process of claim 2, wherein the reaction is carried out at a temperature ranging from 100° to 150° C.

19. The process of claim 2, wherein the fluoride is an alkali metal fluoride, the atomic number of the alkali metal being greater than or equal to that of potassium.

20. The process of claim 2, wherein the reaction is conducted in a dipolar aprotic solvent having a solids content, defined as mass of solid material relative to the total mass, of at least 1/5.

21. The process of claim 20, wherein the solids content is at least ¼.

22. The process of claim 20, wherein the solids content is at least ⅓.

23. The process of claim 20, wherein the dipolar aprotic solvent has a relative dielectric constant $\epsilon$ greater than or equal to 10.

24. The process of claim 23, wherein said dielectric constant is less than or equal to 100 and greater than or equal to 25.

25. The process of claim 20, wherein the dipolar aprotic solvent has a donor index c ranging from 10 to 50, the donor index c being defined as the $\Delta H$, expressed in kilocalories, of the combination of the dipolar aprotic solvent with antimony pentachloride.

26. The process of claim 25, wherein the reaction is carried out at a temperature ranging from 100° to 150° C.

27. The process of claim 2, wherein the suspended solid has a particle size such that its $d_{80}$ (defined as the mesh allowing by weight of the solid to pass through) is at most 100 micrometers.

28. The process of claim 27, wherein said $d_{80}$ is at most 50 μm.

29. The process of claim 27, wherein said $d_{80}$ is at most 20 μm.

30. The process of claim 2, wherein the $d_{20}$ (defined as the mesh allowing 20% by weight of the solid to pass through) of the suspended solid is at least 0.1 μm.

31. The process of claim 30, wherein the $d_{20}$ of the suspended solid is at least 1 μm.

32. The process of claim 2 wherein the fluoride is an alkali metal fluoride and wherein the organic compound in the reaction mixture is a chlorinated compound, the ratio of the alkali metal fluoride to the chlorinated compound ranging from 1:1 to 1.5:1.

33. The process of claim 32, wherein the ratio is about 1.25:1.

34. The process of claim 2, wherein the agitation is conducted in such a way that at least 80% of the solid is in suspension.

35. A process for the synthesis of a fluorinated organic compound comprising reacting an organic compound and a fluoride compound to exchange fluorine for an atom bonded to said organic compound, comprising the following steps:
a) mixing reagents comprising said organic compound and said fluoride compound;
b) applying ultrasonic sound to the mixture formed in step a), thereby causing said organic compound to react with said fluoride compound and exchange fluorine for an atom bonded to said organic compound;
c) separating liquid and solid phases of said mixture after said reaction;
d) treating the liquid phase obtained in step c) to recover both a fluorinated organic compound, and a solution comprising a solvent containing unreacted starting material;
e) recycling the solvent and the unreacted starting material to a).

36. The process of claim 35, further comprising treating the solid phase from step c) to regenerate an alkali metal fluoride and recycling to step a).

37. A method for synthesizing a fluorinated organic compound from an organic starting material by an exchange reaction between halogens, comprising mixing said organic starting material with a reagent and applying ultrasonic sound to cause an exchange reaction whereby a fluorine replaces a halogen from said starting material wherein said reagent contains:
a dipolar aprotic solvent; and,
a solid phase containing an alkali metal fluoride, wherein the solids content, defined as the mass of solid material in said solid phase relative to the total mass of said reagent, is at least 2/5, to effect said reaction with said organic starting material.

38. The method of claim 37, wherein said organic starting material is a chlorinated compound.

39. The method of claim 37, wherein said said exchange reaction forms an aryl fluoride.

40. The method of claim 37, wherein said solids content is at least ½.

41. The method of claim 37, wherein said solids content is at least 2/3.

42. The method of claim 37, wherein said reagent further comprises at least one onium; an alkali metal cation heavier than potassium; or, both said onium and said cation.

43. The method of claim 37, wherein said reagent further comprises a catalytic amount of water.

44. The method of claim 37, wherein said reagent further comprises a catalytic amount of cesium or rubidium halide.

45. The method of claim 37, wherein said reagent further comprises a cation promoter.

* * * * *